United States Patent [19]
Horiuchi et al.

[11] Patent Number: 5,686,251
[45] Date of Patent: Nov. 11, 1997

[54] NAPHTHYRIDINIUM DERIVATIVES

[75] Inventors: Seikoh Horiuchi, Kumamoto; Kazuharu Ienaga; Ko Nakamura, both of Katoh-gun, all of Japan

[73] Assignee: Nippon Zoki Pharmaceutical Co., Ltd., Osaka, Japan

[21] Appl. No.: 510,316

[22] Filed: Aug. 2, 1995

[30] Foreign Application Priority Data

Aug. 5, 1994 [JP] Japan .................................. 6-204517

[51] Int. Cl.$^6$ .................... G01N 33/53; C07D 471/04; C07K 16/00
[52] U.S. Cl. ................... 435/7.1; 435/72; 436/536; 436/547; 530/389.8; 546/122
[58] Field of Search .................... 546/122; 435/7.1, 435/7.2; 436/518, 536, 547, 822; 530/389.8

[56] References Cited

U.S. PATENT DOCUMENTS 5,338,850  8/1994  Nakamura et al. .................. 546/122

FOREIGN PATENT DOCUMENTS

| 0 288 256 A2 | 10/1988 | European Pat. Off. |
| 0 360 258 A2 | 3/1990 | European Pat. Off. |
| 73057 | 3/1994 | Japan |
| WO 89/04491 | 5/1989 | WIPO |
| WO 91/02978 | 3/1991 | WIPO |

OTHER PUBLICATIONS

Sensi, et al., "Advanced Nonenzymatic Glycation Endproducts (Age): Their Relevance To Aging And The Pathogenesis Of Late Diabetic Complications", *Diabetes Research* (1991) 16, 1–9.
Brownlee, M., "Glycation Products and the Pathogenesis of Diabetic Complications", *Diabetes Care*, vol. 15, No. 12, Dec. 1992, pp. 1835–1843.
Brownlee, et al., "Advanced Glycosylation End Products In Tissue And The Biochemical Basis Of Diabetic Complications", *The New England Journal of Medicine*, vol. 318, No. 20, 1315–1321.
Lyons, "Glycation and Oxidation: A Role in the Pathogenesis of Atherosclerosis", *The American Journal of Cardiology*, vol. 71, Feb. 25, 1993, pp. 26B–31B.
Harrington, et al., "A glycation connection", *Nature*, vol. 370, 28 Jul. 1994, pp. 247–248.
Yan, et al., "Non-enxymatically glycated tau in Alzheimer's disease induces neuronal oxidant stress resulting in cytokine gene expression and release of amyloid β-peptide", *Nature Medicine*, vol. 1, No. 7, Jul. 1995, pp. 693–699.
Lamb, et al., "Serum Glycated Albumin and Fructosamine in Renal Dialysis Patients", *Nephron*, 1993; 64:82–88.
Lamb, et al., "Glycated albumin in serum and dialysate of patients on continuous ambulatory peritoneal dialysis", *Clinical Science* (1993) 84, 619–626.
Huber, et al., "Formation of 2-(2-furoyl)-4(5)-(2-furyl)-1H-imidazole in the Maillard Reaction", *Carbohydrate Research*, vol. 182, No. 2, pp. 301–306.
Nakamura, et al., "Crosslines A and B as Candidates for the Fluorophores in Age- and Diabetes-related Cross-linked Proteins, and their Diacetates produced by Maillard Reaction of α-N-Acetyl-L-lysine with o-Glucose", *J. Chem. Soc. Chem. Commun.*, 1992, pp. 992–994.

*Primary Examiner*—Ponnathapura Achutamurthy
*Attorney, Agent, or Firm*—Fisher, Christen & Sabol

[57] ABSTRACT

The present invention provides naphthyridinium derivatives which are effective, for example, in diagnosis of diabetes, diabetic complications, dialysis-related complications, aging, diseases accompanied by aging, etc. and also provides an antibody prepared from said derivative as a hapten. The naphthyridinium derivatives of the present invention are compounds represented by the general formula (I):

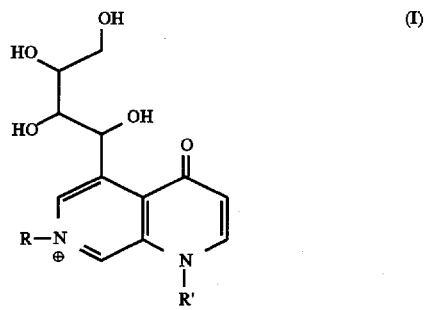

wherein R and R' may be the same or different and are alkyl groups optionally substituted with at least one amino group, at least one protected amino group, at least one carboxyl group, or combinations thereof, and their pharmaceutically accepted salts. It is possible to conduct the diagnosis of diabetes, diabetic complications, dialysis-related complications, aging, diseases accompanied by aging, etc. using a compound of the present invention as an indicator. Moreover, it is possible to utilize a compound of the present invention for the evaluation of the pharmaceutical effect of pharmaceuticals effective for treating diabetes-related diseases, dialysis-related complications, aging and diseases accompanied by aging.

17 Claims, No Drawings

NAPHTHYRIDINIUM DERIVATIVES

FIELD OF THE INVENTION

The present invention relates to novel naphthyridinium derivatives; an antibody prepared from said derivative as a hapten; a method for diagnosis of diabetes, diabetic complications, dialysis-related complications, aging, diseases accompanied by aging, etc. using said derivative or antibody thereof; and a method for evaluation of effects of pharmaceuticals which are effective for treating such diabetes-related diseases, dialysis related complications, aging and diseases which accompany aging.

BACKGROUND OF THE INVENTION

In 1968, glycosylhemoglobin (HbAlc) which is one of the minor components of hemoglobin was identified in vivo and was found to increase in patients diagnosed with diabetes. This discovery has aroused interest in the biological meaning of the Maillard reaction and, particularly in the relationship between aging and diabetes.

The Maillard reaction may be classified into a former stage and latter stage. In the former stage a Schiff base is formed by the condensation reaction between an amino group of a protein and an aldehyde group of a reducing sugar. The Schiff base is stabilized as a result of an Amadori rearrangement. In the latter stage, the former stage product is transferred, after a long series of reactions, to an Advanced Glycation Endproduct (AGE). The latter stage end products are characterized by fluorescence, a color change to brown, and molecular crosslinking. The fluorescence which is known as one of the characteristic changes found in the AGE is significantly higher in diabetic patients than in healthy or non-diabetic persons. The fluorescence is suggested to have a correlation with the onset of diabetic complications such as diabetic nephrosis, arteriosclerosis, nervous disturbance, retinal diseases, cataracts, etc. In addition, since fluorescence of proteins accumulating in the serum increases during dialysis, a relationship between AGE and dialysis-related amyloidosis is suggested. Basic structure for AGE has been analyzed, however, many matters concerning it have not been clarified yet.

U.S. Pat. No. 5,338,850 to Nakamura, et at. discloses pyridinium derivatives which are effective in diagnosis of diabetes, diabetic complications, aging, and diseases accompanied by aging. An antibody prepared from the pyridinium derivatives as a hapten is also disclosed. Evaluation of the effectiveness of pharmaceuticals for the treatment of these ailments is also described.

Meanwhile, as a result of many studies, it has been clarified that diabetic patients are kept under a higher oxygen-stressed condition than normal or non-diabetic persons. It is suggested that this condition is caused by free radicals produced during glycation of proteins and automatic oxidation of glucose. The free radicals also injure the tissues and may become a factor causing diabetic complications and aging.

The present inventors have conducted continued studies on the crosslinked substances, as an indicator to diagnose diabetic complications and aging, which are produced by both reactions of nonenzymatic glycation and oxidation of proteins. As a result thereof, they found novel naphthyridinium derivatives which have different fluorescent characteristics from that of known AGE whereby the present invention has been accomplished. The naphthyridinium derivatives of the present invention are useful in the diagnosis of diabetes, diabetic complications, dialysis-related complications, aging and diseases associated with aging. The naphthyridinium derivatives are also useful for the evaluation of the effectiveness of pharmaceuticals for treatment of diabetes, diabetes related diseases, dialysis related complications, and aging and its accompanying diseases.

SUMMARY OF THE INVENTION

The present invention provides: (a) novel naphthyridinium derivatives and salts thereof, (b) an antibody prepared from said derivative as a hapten, (c) a method for the diagnosis of diabetes, diabetic complications, dialysis-related complications, aging, diseases accompanied by aging, etc. using said derivative, or an antigen or antibody of said derivative, and (d) a method for the evaluation of the effectiveness of pharmaceuticals for treatment of diabetes, diabetes-related diseases, dialysis-related complications, aging, diseases accompanied by aging, etc.

Chemical structures of the naphthyridinium derivatives of the present invention are believed to be highly related to the chemical structures of the Advanced Glycation Endproduct (AGE) of the Maillard reaction. The derivatives are useful for detecting Maillard reaction type products associated, for example, with diabetes and aging.

For example, the antibodies of the present invention may be prepared by reacting a naphthyridinium derivatives with a carrier protein to stimulate antibody production in vivo. The antibodies thus produced may be used to detect antigen or latter-stage, fluorescent Maillard reaction type products or AGE associated with or resulting from diabetes, diabetic complications, dialysis-related complications, aging, and diseases associated with aging. The naphthyridinium derivatives of the present invention may be used to detect antibodies associated with: (a) diabetes or aging, (b) dialysis-related complications, or (c) diseases which accompany diabetes or aging. Evaluation of the effectiveness of pharmaceuticals or therapeutic agents for the treatment or prevention of these ailments may be performed, for example, by using the antibodies of the present invention to detect any decreases or increases in the amount of antigens or AGE which result from the treatment.

The naphthyridinium derivatives of the present invention are represented by the structural formula (I) and pharmaceutically acceptable salts thereof:

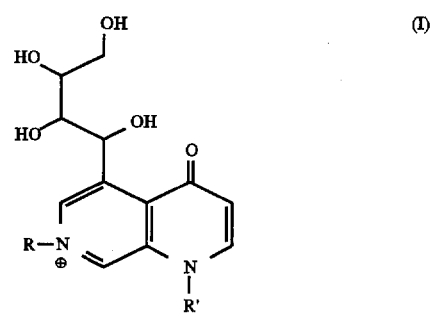

wherein R and R' may be the same or different and are unsubstituted alkyl groups, or alkyl groups substituted with at least one member selected from the group consisting of amino, protected amino, and carboxyl groups.

Derivatives of the present invention may be produced by a process comprising combining a compound of the formula R—NH$_2$ or R'—NH$_2$ (wherein R and R' have the same meaning as described above) with a sugar, such as a hexose or an oligosaccharide consisting of at least one hexose to obtain a mixture, and permitting the mixture to stand for a sufficient mount of time to obtain one or more of the derivatives, and recovering the derivatives from the reaction mixture.

DETAILED DESCRIPTION OF THE INVENTION

A novel naphthyridinium derivative of the present invention is a compound represented by the following general formula (I):

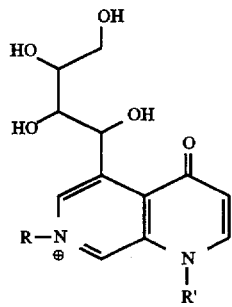

wherein R and R' may be the same or different and represent an alkyl group, or an alkyl group substituted with an amino, protected amino and/or carboxyl substituent.

The optionally substituted alkyl groups R and R' in the above general formula (I) may be acyclic and may have a linear or branched structure. The alkyl groups may also be cycloalkyl groups.

Examples of the preferred alkyl for R and R' in the above general formula (I) are linear or branched alkyl groups having 1 to 6 carbon atom(s) such as methyl, ethyl, propyl, isopropyl, butyl, isobutyl, sec-butyl, tert-butyl, pentyl, isopentyl, neopentyl, tert-pentyl and hexyl groups.

The above-described alkyl groups for R and R' may be substituted with at least one member selected from the group consisting of amino, protected amino, and carboxyl groups. With regard to the protective groups for the amino group, those which are commonly used in the field of peptide synthesis, may be utilized. They are, for example, formyl, acetyl, tosyl, benzyloxycarbonyl, p-methoxybenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, tert-butoxycarbonyl, tert-amyloxycarbonyl, p-biphenylisopropyloxycarbonyl and diisopropylmethyloxycarbonyl.

Among the substances of the present invention represented by the general formula (I), naphthyridinium derivatives wherein R and R' are alkyl having amino and/or carboxyl can be easily combined with a carrier protein as haptens and are particularly useful for the preparation of an antibody of the present invention. As to a carrier for combining with a hapten for preparation of the antibody of this invention, the commonly used carriers such as protein (e.g. serum albumin, keyhole lympet hemocyanin) and polymers (e.g. polylysine) may be used.

The naphthyridinium derivatives of the present invention include salts of the compounds represented by the general formula (I). The salts include pharmaceutically acceptable salts with at least one metal, acid, or base. Exemplary salts are alkali metal salts such as sodium, potassium and lithium salts; alkali earth metal salts such as magnesium, calcium and barium salts; and salts of other metals such as aluminum. Further examples are addition salts with acids such as hydrochloric acid, sulfuric acid, nitric acid, hydrobromic acid, phosphoric acid, perhydrochloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphtalenesulfonic acid, sulfanilic acid and trifluoroacetic acid; and salts of ammonia or of organic bases such as amines.

The salts of the present invention can be manufactured by conventional methods from the naphthyridinium derivatives of the present invention in free form and vice versa.

When the substances of the present invention have stereoisomers such as cis-trans isomers, optical isomers, conformational isomers, etc., the present invention includes any of such stereoisomers.

The compounds of the present invention may be produced, for example, by reacting a compound of the formula R—$NH_2$ or R'—$NH_2$ (amine component; wherein R and R' are the same groups as described above) with a sugar, for example, a hexose such as glucose, fructose, galactose, mannose or deoxyglucose, a heptose such as sedoheptulose, an amino sugar such as glycosamine or galactosamine, or an oligosaccharide such as saccharose, to obtain the compound of the present invention. There is no particular restriction for the reaction conditions such as reaction temperature, reaction time, pH, etc. and they may be readily established. For example, an easy procedure is allowing the reaction mixture to stand at room temperature and atmospheric pressure. However, the reaction can be accelerated by heating and the like. Temperatures up to about 40° C. for about three to nine weeks may, for example, be used to obtain the compounds of the present invention.

The substances of the present invention prepared as such may be purified by conventional means such as distillation, chromatography, recrystallization, etc. and identified by means of NMR, mass analysis, fluorescence spectrum, etc.

The present invention is further illustrated by the following examples wherein all parts, percentages, and ratios are by weight and all temperatures are in ° C. unless otherwise indicated:

EXAMPLE 1

28.2 g of α-N-acetyl-L-lysine and 27 g of glucose were dissolved in 750 ml of 250 mM phosphate buffer (pH: 7.4) and allowed to stand at 37° C. for 8 weeks. The reaction solution was added to an ion-exchange resin column of the sulfonate type/DIAION PK-216 H-form (Mitsubishi Kasei Corp.) and then the column was thoroughly washed with water. The fraction eluted by 2N aqueous ammonia was concentrated to dryness. This was further separated by a DEVELOSIL ODS LOP-45S column (Nomura Chemical Corp.). The methanol content in the elution solvent is stepwisely increased, for example, in the order of 0.2% trifluoro acetic acid (TFA), 10% methanol/0.2% TFA and 20% methanol/0.2% TFA. The fraction eluted by the solvent containing 20% methanol was purified by a reversed phase HPLC/STR ODS-II column (Shimadzu Techno-Research Inc.) to give 1,7-bis[6-(N-acetyl-L-norleucyl)]-5-(1,2,3,4- tetrahydroxybutyl)-1,4-dihydro-4-oxo-1,7-naphthyridinium (TFA salt form).

Analytical results obtained with $^{13}$C-NMR (100 MHz, $D_2O$), $^1$H-NMR (400 MHz, $D_2O$) and mass analysis were:

$^{13}$C-NMR (100 MHz, $D_2O$): 177.1(s), 177.1(s), 175.8(s), 175.6(s), 149.5(s), 143.8(s), 137.9(d), 137.6(d), 122.7(s), 120.2(s), 110.0(d), 93.0(d), 74.0(d), 71.6(d), 66.6(d), 64.6 (d), 57.6(t), 54.1(d), 54.1(d), 48.4(t), 32.0(t), 31.7(t), 30.1(t), 30.1(t), 23.8(t), 23.2(t), 23.2(q), 23.2(q)

$^1$H-NMR (400 MHz, $D_2O$): 8.35(1H, d,J=7 Hz), 7.97(1H, d,J=7 Hz), 7.95(1H, s), 6.77(1H,s), 5.46(1H,s), 4.65(1H,m), 4.55(1H,m), 4.54(1H, d,J=9 Hz), 4.37(2H,t,J=6 Hz), 4.37 (1H, m), 4.25(1H,m), 4.0–4.1(2H, m), 3.71(1H, dd,J=7, 12 Hz), 2.02(3H, s), 1.96(3H, s), 1.25–2.1(6H,m)

Mass analysis (SIMS, Glycerol): M+ (m/z)=609

EXAMPLE 2

41.2 g of γ-aminobutyric acid and 72 g of glucose were dissolved in 1000 ml of 250 mM phosphate buffer (pH: 7.4) and allowed to stand at 37° C. for 4 weeks. The reaction solution was added to an XAD-2 column (Organo Corp.), and each fraction (80 ml) was collected and analyzed using a reversed phase HPLC/STR ODS-II column. The fraction containing the objective substances was concentrated, and then further separated by reversed phase column chromatography using a YMC-GEL ODS-AM 120 S50 column (YMC Co., Ltd.). The obtained fractions were analyzed using the said reversed phase HPLC. The fractions containing the objective substances were collected and concentrated, and then purified by removing excess TFA to give 1,7-bis(3-carboxypropyl)-5-(1,2,3,4-tetrahydroxybutyl)-1,4-dihydro-4-oxo-1,7-naphthyridinium (TFA salt form).

Analytical results obtained with $^{13}$C-NMR (100 MHz, $D_2O$), $^1$H-NMR (400 MHz, $D_2O$) and mass analysis were:

$^{13}$C-NMR (100 MHz, $D_2O$): 180.2(s), 180.2(s), 149.3(s), 143.9(s), 137.9(d), 137.8(d), 122.8(s), 120.1(s), 110.0(d), 92.9(d), 74.0(d), 71.5(d), 66.5(d), 64.6(t), 57.2(t), 48.1(t), 34.0(t), 31.5(t), 28.9(t), 27.1(t)

$^1$H-NMR (400 MHz, $D_2O$): 8.37(1H, d,J=7 Hz), 7.97(1H, d,J=7 Hz), 7.96(1H, s), 6.81(1H,s), 5.45(1H, s), 4.70(1H,m), 4.52(1H,m), 4.52(1H, d,J=9 Hz), 4.39(2H,t,J=7 Hz), 3.99 (1H,d,J=12 Hz), 3.98(1H, dd,J=7,9 Hz), 3.69(1H,br.dd,J=7, 12 Hz), 2.15–2.55(8H,m)

Mass analysis (SIMS, Glycerol): M+ (m/z)=439

EXAMPLE 3

α-N-tosyl-L-lysine was used as an amine component, and the mixing reaction with glucose was carried out in the same manner as in Example 2. The separation and purification were also performed as in Example 2 to give 1,7-bis[6-(N-tosyl-L-norleucyl)]-5-(1,2,3,4-tetrahydroxybutyl)-1,4-dihydro-4-oxo-1,7-naphthyridinium (TFA salt form).

Analytical results obtained with $^1$H-NMR (400 MHz, $D_2O/CD_3OD$) were:

$^1$H-NMR (400 MHz, $D_2O/CD_3OD$): 8.40(1H,d,J=7 Hz), 8.00(1H,d,J=7 Hz), 7.98(1H, s), 7.66(2H,d,J=8 Hz), 7.63 (2H, d,J=8 Hz), 7.35(2Hd,J=8 Hz), 7.34(2H,d,J=8 Hz), 6.73(1H,s), 5.41(1H,s), 4.65(1H,m), 4.52(1H,m), 4.52(1H, d,J=9 Hz), 4.38(2H,t,J=7 Hz), 3.99(1H,br.d,J=12 Hz), 3.98 (1H, dd,J=7,9 Hz), 3.70(1H,m), 3.69(1H,br.dd,J=7,12 Hz), 3.64(1H,m), 2.40(3H,s), 2.40(3H,s), 1.3–2.0(12H,m)

EXAMPLE 4

25 g of α-N-tert-butoxycarbonyl-ε-N-benzyloxycarbonyl-L-lysine was dissolved in 300 ml of methanol and reduced using a palladium-carbon catalyst in an atmosphere of hydrogen to remove the benzyloxycarbonyl group. 16.2 g of the resulting α-N-tert-butoxycarbonyl-L-lysine and 12.1 g of glucose were dissolved in 335 ml of 250 mM phosphate buffer (pH: 7.3) and allowed to stand at 37° C. for 24 days. After the reaction mixture was separated and purified using a YMC-GEL ODS-AM 120 S50 column and a STR ODS-II column, the purified component was dissolved in TFA and allowed to stand for 30 minutes to remove the tert-butoxycarbonyl group to give 1,7-bis[6-(L-norleucyl)]-5-(1,2,3,4-tetrahydroxybutyl)-1,4-dihydro-4-oxo-1,7-naphthyridinium (TFA salt form).

The antibody to the naphthyridinium derivatives of the present invention was prepared by a conventional method, i.e., the substance combined with keyhole lympet hemocyanin was administered to immunize a rabbit. The obtained antibody significantly reacted with various glycated proteins. However, it did not react with normal proteins which were not glycated. Additionally, it has been found that the antibody reacts with extracts of human lens and the reaction increases according to aging. The substance of this invention shows immun-cross reaction with an antibody which is prepared by using AGE-proteins as antigens.

Several candidates as Advanced Glycation Endproduct (AGE) have been shown and the concerned studies are continuing. One of the candidates, a novel pyridinium derivative, was disclosed in the Laid-Open Japanese Patent Publication Hei-07/73057 and corresponding U.S. Pat. No. 5,338,850. The publication showed that the excitation wavelengths of the pyridinium derivatives are from 370 nm to 380 nm. On the other hand, the substances of the present invention have different fluorescent characteristics from that of known AGE. Since the excitation wavelengths of the substances of this invention are about 325 nm, the instant substances cannot be detected by fluorescent analysis using the said excitation wavelengths as reported above. The oxidation reaction is not needed for the production of said pyridinium derivatives. However, the substances of the present invention may be produced by both reactions of glycation and oxidation from consideration of the characteristic structure. Therefore, the instant substances are highly focused as a novel candidate for AGE.

As mentioned above, since many studies clarified that diabetic patients are kept under a higher oxygen-stressed condition than normal or non-diabetic persons, the crosslinked substances produced by both reactions of glycation and oxidation in the present invention are highly useful as a new indicator to diagnose diabetic complications and aging.

Accordingly, it is possible to conduct diagnosis of diabetes, diabetic complications (e.g. diabetic nephrosis, diabetic arteriosclerosis, diabetic nervous disturbance, diabetic cataract, diabetic retinal diseases, diabetic minute blood vessel disturbance, etc.), dialysis-related complications, aging and diseases accompanied by aging using a compound of the present invention as an indicator. Moreover, it is possible to conduct an evaluation of the pharmaceutical effect in test systems which are in vitro and in vivo using a compound of the present invention as an indicator. For example, the antibodies of the present invention may be used to detect any decreases or increases in the amount of antigens or Advanced Glycation Endproducts which result from the treatment. In addition, the antibody prepared from the compound of the present invention as a hapten can be utilized immunochemically and immunohistochemically in the above-mentioned diagnosis and evaluation and are very highly useful.

What is claimed is:

1. A naphthyridinium derivative represented by the general formula (I):

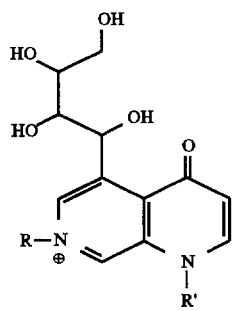

wherein R and R' may be the same or different and each of R and R' is an alkyl group, or an alkyl group substituted with at least one member selected from the group consisting of amino, protected amino and/or carboxyl groups, and pharmaceutically acceptable salts of the derivatives.

2. A naphthyridinium derivative as claimed in claim 1 wherein R and R' is an alkyl group having at least one amino substituent.

3. A naphthyridinium derivative as claimed in claim 1 wherein R and R' is an alkyl group having at least one protected amino substituent.

4. A naphthyridinium derivative as claimed in claim 1 wherein R and R' is an alkyl group having at least one carboxyl substituent.

5. A naphthyridinium derivative as claimed in claim 1 wherein R and R' is an alkyl group having at least one protected amino substituent and at least one carboxyl substituent.

6. A naphthyridinium derivative as claimed in claim 1 wherein said alkyl group or said alkyl group which is substituted has 1 to 6 carbon atoms.

7. An antibody prepared from a naphthyridinium derivative as claimed in claim 1 as a hapten.

8. A method for the diagnosis of diabetes, diabetic complications, dialysis-related complications, aging and diseases accompanied by aging comprising using a naphthyridinium derivative of claim 1 as an indicator.

9. A method for the diagnosis of diabetes, diabetic complications, dialysis-related complications, aging and diseases accompanied by aging comprising using an antibody which is prepared from a naphthyridinium derivative of claim 1 as a hapten.

10. A method for the evaluation of the effectiveness of pharmaceuticals as therapeutic agents for diabetes, diabetic complications, and for dialysis-related complications, as preventive agents for aging and as therapeutic agents for diseases accompanied by aging comprising using a naphthyridinium derivative of claim 1 as an indicator.

11. A method for the evaluation of the effectiveness of pharmaceuticals as therapeutic agents for diabetes, diabetic complications, and for dialysis-related complications, as preventive agents for aging and as therapeutic agents for diseases accompanied by aging comprising using an antibody which is prepared from a naphthyridinium derivative of claim 1 as a hapten.

12. A method for the diagnosis of diabetes and diabetic complications comprising detecting antigens or Advanced Glycation Endproducts associated with or resulting from diabetes or diabetic complications with an antibody as claimed in claim 7.

13. A method for the evaluation of the effectiveness of a pharmaceutical for the treatment of diabetes or diabetic complications comprising detecting any changes caused by the treatment in the amount of antigens or Advanced Glycation Endproducts which are associated with or result from diabetes or diabetic complications wherein said detection is achieved using an antibody of claim 7.

14. A method for the diagnosis of aging and diseases associated with aging comprising detecting antigens or Advanced Glycation Endproducts associated with or resulting from aging or diseases associated with aging with an antibody as claimed in claim 7.

15. A method for the evaluation of the effectiveness of a pharmaceutical for the prevention of aging or as a therapeutic agent for diseases associated with aging comprising detecting any changes resulting from administration of said pharmaceutical in the amount of antigens or Advanced Glycation Endproducts which are associated with or result from aging or diseases associated with aging wherein said detection is achieved using an antibody of claim 7.

16. An antibody obtained using a naphthyridinium derivative as claimed in claim 1 wherein the antibody is an indicator for the diagnosis of diabetes, diabetic complications, dialysis-related complications, aging or diseases accompanied by aging, and is an indicator for the evaluation of the effects of pharmaceuticals or therapeutic agents for diabetes, diabetic complications, dialysis-related complications, the effects of preventative agents for aging, or the effects of therapeutic agents for diseases accompanied by aging.

17. A naphthyridinium derivative as claimed in claim 1 which has an excitation wave length of about 325 nm.

* * * * *